(12) United States Patent
Pringle

(10) Patent No.: US 11,554,193 B2
(45) Date of Patent: Jan. 17, 2023

(54) BIOAEROSOL INACTIVATOR UVC ANTIMICROBIAL REACTOR

(71) Applicant: Luminys Systems Corp., North Hollywood, CA (US)

(72) Inventor: David A. Pringle, North Hollywood, CA (US)

(73) Assignee: LUMINYS SYSTEMS CORP., North Hollywood, CA (US)

( * ) Notice: Subject to any disclaimer, the term of this patent is extended or adjusted under 35 U.S.C. 154(b) by 0 days.

(21) Appl. No.: 17/191,590

(22) Filed: Mar. 3, 2021

(65) Prior Publication Data
US 2022/0280675 A1 Sep. 8, 2022

(51) Int. Cl.
| A61L 9/20 | (2006.01) |
| B01D 53/00 | (2006.01) |
| F24F 13/24 | (2006.01) |

(52) U.S. Cl.
CPC ............. *A61L 9/20* (2013.01); *B01D 53/007* (2013.01); *F24F 13/24* (2013.01); *A61L 2209/10* (2013.01); *A61L 2209/16* (2013.01); *B01D 2259/804* (2013.01)

(58) Field of Classification Search
CPC .......... A61L 9/20; B01D 53/007; F24F 13/24
See application file for complete search history.

(56) References Cited

U.S. PATENT DOCUMENTS

| 5,399,319 | A * | 3/1995 | Schoenberger | ............ A61L 9/20 422/121 |
| 11,052,169 | B1 * | 7/2021 | Pisharodi | .................. B64F 5/30 |
| 2001/0048889 | A1 * | 12/2001 | Palestro | .................... A61L 9/20 422/4 |
| 2006/0057020 | A1 * | 3/2006 | Tufo | ......................... F24F 3/16 422/24 |
| 2008/0199354 | A1 * | 8/2008 | Gordon | ................ A61N 5/0613 422/24 |
| 2018/0084956 | A1 * | 3/2018 | Childress | ................... A61L 9/20 |
| 2018/0133355 | A1 * | 5/2018 | Kirschman | ........... A61L 2/0023 |
| 2018/0361007 | A1 | 12/2018 | Caffrey | |

* cited by examiner

*Primary Examiner* — Kevin Joyner
(74) *Attorney, Agent, or Firm* — Ladas & Parry, LLP

(57) ABSTRACT

An apparatus for inactivating bioaerosol, comprising an enclosure having lumen walls forming a lumen, said lumen having a lumen input opening and a lumen output opening; a ventilator arranged for forcing an air flow through said lumen; in a cleaning section of said lumen, a source of ultraviolet light arranged to irradiate with ultraviolet light all the air passing through said lumen along a length of said cleaning section; an output muffler arranged for reducing a noise of said air flow in output of said lumen output opening; and a downstream turn section of said lumen, downstream said cleaning section of said lumen, arranged for changing a direction of said air flow such that no ultraviolet light in said cleaning section of said lumen is detectable at said lumen output opening.

21 Claims, 5 Drawing Sheets

BIOAEROSOL INACTIVATOR UVC ANTIMICROBIAL REACTOR

TECHNICAL FIELD

This presentation is directed in general to the field of air purifiers and in particular to an apparatus and corresponding method for sterilizing air. The present invention relates to apparatuses and methods for killing bacteria or fungal spores and inactivating viruses aerosolized in air (i.e. inactivating bioaerosol) to prevent aerosol transmission of disease.

BACKGROUND

An infectious aerosol is a collection of pathogen-laden water droplets or other particles in air. Aerosol particles may deposit onto or be inhaled by a person and contaminate that person. Infectious aerosol is generated by or from an infectious person. If the pathogen remains viable in the environment for some period of time, and the target tissues in which the pathogen initiates infection are accessible to the aerosol, aerosol transmission can take place. Aerosol transmission was for example evaluated for Severe Acute Respiratory Syndrome coronavirus and norovirus and was discussed for *Mycobacterium tuberculosis*, influenza, and Ebola virus.

An air purifier or air cleaner is a device which removes contaminants from the air in a room to improve indoor air quality. Commercially graded air purifiers can be manufactured as either stand-alone units or can be affixed to an air handler unit (AHU) or to an HVAC unit found in the medical, industrial, and commercial industries. Known air purifiers generally use filtration, with air being forced through a filter that physically captures bioaerosol and particles. Sources of ultraviolet light can be used to inactivate the bioaerosols captured by the filters. Drawbacks of filter-based air purifiers are that the filter needs to be cleaned regularly and also that forcing the air through the filter consumes a lot of energy, slows down the air flow, and is very noisy above given air speed. Such devices are not suitable for silently and efficiently inactivating bioaerosol that would be present in the air of a room.

US20180361007 discloses a battery-operated ultraviolet germicidal irradiation device adapted to be mounted in an air distribution duct, for reducing air-borne contaminants within air passing through the air-distribution duct. The battery-powered device is provided to be mounted in the duct by means of a permanent magnet, mounting clip or flange. The device needs to be mounted close to the discharge opening of the duct so as to be accessible to change the battery, which makes it difficult to prevent that at least a portion of the ultraviolet light emitted by the device can be seen from outside of the discharge opening of the duct. As the device is mounted in the duct after the duct is installed, it is further difficult to know where to attach the device in the duct to ensure that all the air that passes through the duct is irradiated with ultraviolet light. Such devices are not suitable for silently, safely or and efficiently inactivating bioaerosol that would be present in the air of a room.

There exists a need, for example in the movie industry, for a device and corresponding method that allow purifying noiselessly a large quantity of air such as the air of a movie set, while preventing any leak of ultraviolet light to the outside of the device.

SUMMARY

To address one or more of the above-deficiencies of the prior art, an embodiment described in this presentation relates to An apparatus for inactivating bioaerosol, comprising: an enclosure having lumen walls forming a lumen, said lumen having a lumen input opening and a lumen output opening; a ventilator arranged for forcing an air flow through said lumen; in a cleaning section of said lumen, a source of ultraviolet light arranged to irradiate with ultraviolet light all the air passing through said lumen along a length of said cleaning section; an output muffler arranged for reducing a noise of said air flow in output of said lumen output opening; and a downstream turn section of said lumen, downstream said cleaning section of said lumen, arranged for changing a direction of said air flow such that no ultraviolet light in said cleaning section of said lumen is detectable at said lumen output opening.

According to embodiments of this presentation, said output muffler comprises a sound damping material lining the lumen walls of an output muffler section of the lumen, downstream of said cleaning section of said lumen.

According to embodiments of this presentation, said ventilator is arranged such that said air flow has a debit comprised between 200 cfm and 1600 cfm, said cleaning section of the lumen and said source of ultraviolet light are arranged such that any particle traveling through cleaning section 26 receives an energy of between 40 and 160 microwatt·second per cm2 of surface of the particle, and said output muffler is arranged such that the apparatus produces a noise comprised between 18 dB and 35 dB. These features allow killing or inactivating between 99.9999% and 99.99% of the bacteria, fungal spores or viruses aerosolized in the air flow.

According to embodiments of this presentation, said downstream turn section of said lumen comprises a first elbow section that changes the direction of the airflow by 180 degrees between said cleaning section of said lumen and said lumen output opening.

According to embodiments of this presentation, said output muffler comprises a sound damping material lining the lumen walls of an output muffler section of the lumen, between said first elbow section and said lumen output opening.

According to embodiments of this presentation, the apparatus comprises a flexible output air duct having a first air duct input opening and a second air duct output opening; the first air duct input opening being connected to the lumen output opening, such that the air flow is output from the first air duct output opening.

According to embodiments of this presentation, the apparatus comprises an input muffler arranged for reducing a noise of said air flow in input of said lumen input opening.

According to embodiments of this presentation, an upstream turn section of said lumen, upstream said cleaning section of said lumen, is arranged for changing a direction of said air flow such that no ultraviolet light in said cleaning section of said lumen is detectable at said lumen input opening.

According to embodiments of this presentation, said upstream turn section of said lumen comprises a second elbow section that changes the direction of the airflow by 180 degrees between said lumen input opening and said cleaning section of said lumen.

According to embodiments of this presentation, said ventilator is arranged upstream of said upstream turn section of the lumen.

According to embodiments of this presentation, the apparatus comprises an input muffler arranged for reducing a noise of said air flow in input of said lumen input opening, said input muffler comprising a sound damping material lining the lumen walls of an input muffler section of the lumen, between said upstream turn section and said lumen input opening.

According to embodiments of this presentation, the apparatus comprises a flexible input air duct having a second air duct input opening and a second air duct output opening; the second air duct output opening being connected to the lumen input opening, such that said air flow is input from the second air duct input opening.

According to embodiments of this presentation, the ventilator is arranged upstream of said cleaning section of said lumen.

According to embodiments of this presentation, the ventilator is arranged in a sound muffling enclosure.

According to embodiments of this presentation, the source of ultraviolet light comprises at least one ultraviolet light bulb arranged on a first wall portion of said cleaning section of said lumen, and a material reflective of ultraviolet light arranged on a second wall portion of said cleaning section of said lumen.

According to embodiments of this presentation, the lumen walls of said cleaning section of said lumen form a juxtaposition of flat rectangular walls parallel to an axis of the lumen, such that any radial cross-section of cleaning section is polygonal, each of said rectangular walls having a surface reflective of ultraviolet light and at least one of said rectangular walls bearing an ultraviolet light tube lamp.

According to embodiments of this presentation, at least one portion of the lumen walls within said cleaning section of said lumen comprise a wall opening with a mobile lid having a closed position A and an open position B, wherein: when said lid is in the closed position A, said ultraviolet light does not exit said lumen through said wall opening, and when said lid is in the open position B, said ultraviolet light exits said lumen through said wall opening.

Other embodiments of this presentation relate to a method for inactivating bioaerosol, the method comprising: providing an enclosure having lumen walls forming a lumen, said lumen having a lumen input opening and a lumen output opening; with a ventilator, forcing an air flow through said lumen; in a cleaning section of said lumen, irradiate with ultraviolet light all the air passing through said lumen along a length of said cleaning section; with an output muffler, reducing a noise of said air flow in output of said lumen output opening; and providing a downstream turn section of said lumen, downstream said cleaning section of said lumen, said downstream turn section being arranged for changing a direction of said air flow such that no ultraviolet light in said cleaning section of said lumen is detectable at said lumen output opening.

According to embodiments of this presentation, the method comprises arranging said ventilator such that said air flow has a debit comprised between 200 cfm and 1600 cfm, arranging said cleaning section of the lumen and said source of ultraviolet light such that any particle traveling through cleaning section 26 receives an energy of between 40 and 160 microwatt·second per cm2 of surface of the particle, and arranging said output muffler such that the apparatus produces a noise comprised between 18 dB and 35 dB. These features allow killing or inactivating between 99.9999% and 99.99% of the bacteria, fungal spores or viruses aerosolized in the air flow.

According to embodiments of this presentation, the method comprises using an input muffler to reduce a noise of said air flow in input of said lumen input opening, and providing an upstream turn section of said lumen, upstream said cleaning section of said lumen, for changing a direction of said air flow such that no ultraviolet light in said cleaning section of said lumen is detectable at said lumen input opening.

Although specific advantages have been enumerated above, various embodiments may include some, none, or all of the enumerated advantages. Additionally, other technical advantages may become readily apparent to one of ordinary skill in the art after review of the following figures and description.

BRIEF DESCRIPTION OF THE DRAWINGS

For a more complete understanding of this presentation and its advantages, reference is now made to the following description taken in conjunction with the accompanying drawings, in which like reference numerals represent like parts. The drawings are not to scale, unless specifically provided.

DETAILED DESCRIPTION

It should be understood at the onset that, although example embodiments are illustrated below, the present technology may be implemented using any number of techniques, whether currently known or not. The present technology should in no way be limited to the example implementations, drawings, and techniques illustrated below. Additionally, the drawings are not necessarily drawn to scale.

Figure 1:
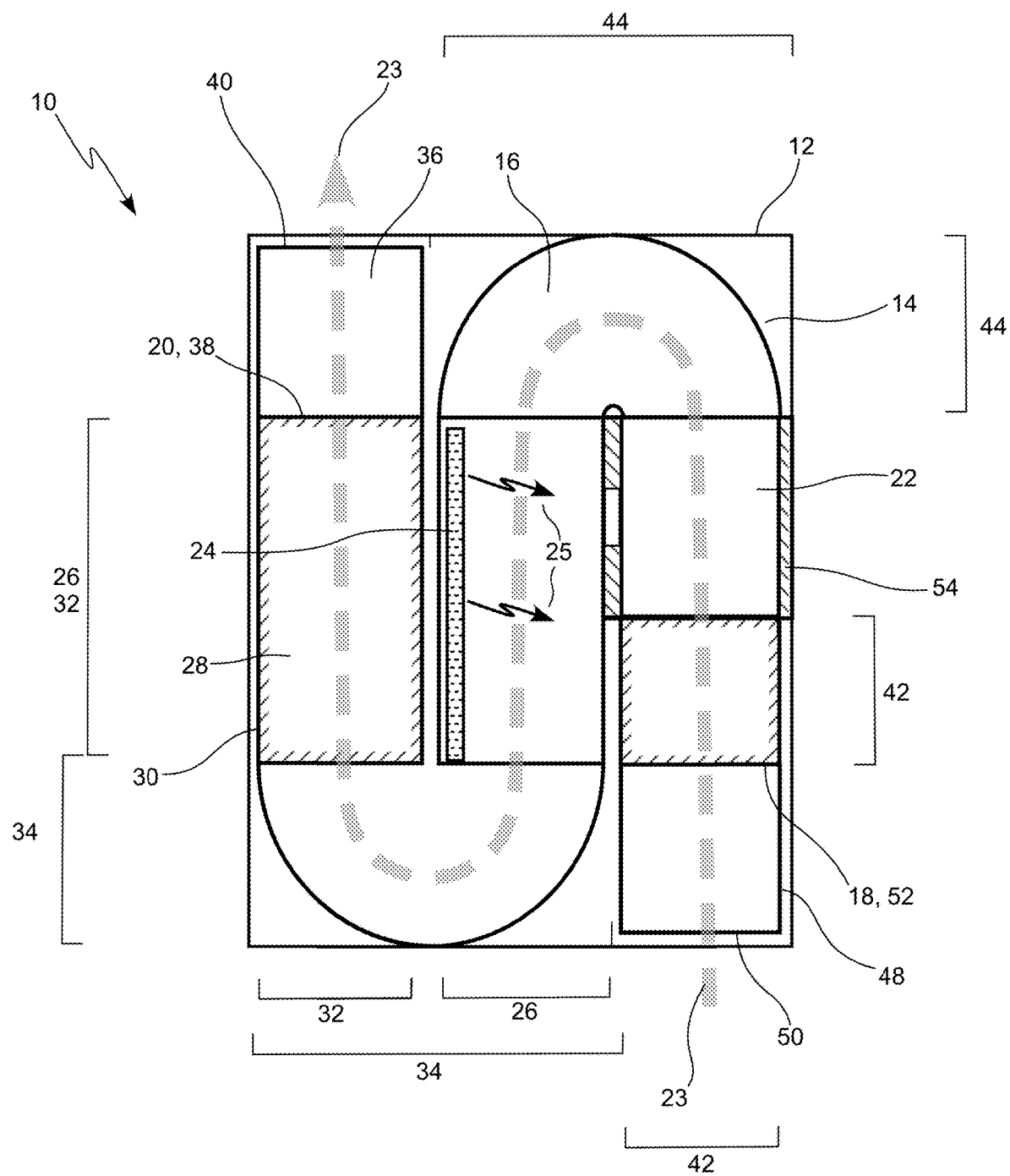
FIG. 1 illustrates an apparatus according to embodiments of this presentation.

FIG. 1 illustrates an apparatus 10 for bioaerosol inactivation in air according to embodiments of this presentation. Apparatus 10 comprises an enclosure 12 having lumen walls 14 forming a lumen 16, said lumen having a lumen input opening 18 and a lumen output opening 20. Apparatus 10 further comprises a ventilator 22 arranged for forcing an air flow 23 through said lumen 16; and, in a section 26 of the lumen 16 that will hereafter be called "cleaning section" of the lumen, a source 24 of ultraviolet light 25 arranged to irradiate with ultraviolet light all the air passing through said lumen 16 along a length of said cleaning section 26. Embodiments of the cleaning section 26 of lumen 16 are detailed hereafter, for example in relation with FIGS. 3 and 4.

According to embodiments of this presentation, apparatus 10 further comprises an output muffler 28 arranged for reducing a noise of the air flow 23 in output of the lumen output opening 20, as well as a downstream turn section 34 of lumen 16, arranged downstream the cleaning section 26 of lumen 16 and arranged for changing a direction of the air flow 23 such that no ultraviolet light emitted in cleaning section 26 is detectable at the lumen output opening 20. According to this presentation, it is considered that no ultraviolet light emitted in cleaning section 26 is detectable at a lumen opening if only 0.3% or less of the ultraviolet light radiation in output of the cleaning section 26. In an example, the ultraviolet light radiation in output of the cleaning section 26 is of 4500 microwatt/cm2 and the ultraviolet light output at opening 20 is 10 microwatt/cm$^2$ or less. According to embodiments of this presentation, 0.3% or less of the ultraviolet light radiation in output of the cleaning section 26 is output from opening 20.

According to embodiments of this presentation, the downstream turn section 34 of lumen 16 comprises a first elbow section 34, which changes the direction of the airflow 23 by 180 degrees between the cleaning section 26 of said lumen and the lumen output opening 20. Turn section 34 is shown as comprising only a curved section, but it can comprise also one or more straight sections in combination with one or more curved sections. With the exception of the cleaning section 26, which is described hereafter, the inner walls of lumen 16 are non-reflective to UV light to help preventing UV light from reflecting its way out of apparatus 10. According to embodiments of this presentation, with an elbow section having non-reflective inner walls 0.05% or less of the ultraviolet light radiation in output of the cleaning section 26 is output from opening 20.

Output muffler 28 for example comprises a sound damping material 30 lining the lumen walls 14 of an output muffler section 32 of the lumen 16, downstream of said cleaning section 26 of said lumen, for example between the elbow section 34 and said lumen output opening 20. Sound damping material 30 can comprise foam, felt or any appropriate material. According to embodiments of this presentation, with a muffler and an elbow section with non-reflective walls, 0% of the ultraviolet light radiation in output of the cleaning section 26 is output from opening 20.

The Inventor has noted that an apparatus such as the apparatus 10 of FIG. 1 allows purifying air, by killing or inactivating between 99.9999% and 99.99% of the bacteria, fungal spores or viruses aerosolized in an air flow 23 having a debit comprised between 200 cfm (cubic feet per minute) and 1600 cfm, while producing a noise in output of output muffler 28 comprised between 18 dB and 35 dB (preferably between 18 dB and 25 dB). According to embodiments of this presentation, the power of the UV light source can be such that any particle traveling through cleaning section 26 receives an energy of between 40 and 160 microwatt·second per cm2 of surface of the particle. According to embodiments of this presentation, the lower the speed of air is, the longer each molecule of air spends time in the cleaning section and therefore receives a higher dosage of UV radiation. According to embodiments of this presentation, to add one more 9 to the 99.99% requires twice the UV dosage. Thus for 99.9999% one needs to double the UV dosage twice (i.e. by either increasing the UV power or reducing the speed of air). According to embodiments of this presentation, the minimum time spent by a molecule of air in cleaning section is comprised between 0.08 s (with a UV intensity of 44000 microwatt/cm2) and 0/25 s (with a UV intensity of 20000 microwatt/cm2))

According to embodiments of this presentation, the sound damping material 30 lining the lumen walls 14 can comprise recesses or grooves or protrusions arranged, for example as in a gun barrel, to cause air flow 23 to rotate around a longitudinal axis of the lumen.

Optionally apparatus 10 comprises a flexible output air duct 36 with a first air duct input opening 38 and a second air duct output opening 40. The first air duct input opening 38 can be connected to the lumen output opening 20, such that air flow 23 is output from the first air duct output opening 40. Flexible air duct 36 for example allows to direct the air flow 23 output by the apparatus toward a preferred direction. Flexible air duct 36 can also be extendable. Flexible air duct 36 can be particularly useful when it is desired to bathe a particular portion of a room or movie set with bioaerosol-free air (i.e. air free of aerosolized bacteria, viruses or fungal spores). According to embodiments of this presentation (not shown), the output muffler 28 or an additional output muffler can be arranged in output of the flexible air duct 36.

An upstream turn section 44 of lumen 16 can also be provided upstream the cleaning section 26 of lumen 16. Such upstream turn section can then be arranged for changing a direction of the air flow 23 such that no ultraviolet light emitted in the cleaning section 26 of the lumen 16 is detectable from the lumen input opening 18. According to embodiments of this presentation, such upstream turn section 44 can comprise a second elbow section 44, which changes the direction of the airflow 23 by 180 degrees between the lumen input opening 18 and the cleaning section 26 of said lumen 16.

Optionally, apparatus 10 can comprise an input muffler 42 arranged for reducing a noise of the air flow 23 that enters the input opening 18 of lumen 16. Input muffler 42 can comprise a sound damping material 46 lining the lumen walls of an input muffler section 42 of the lumen 16, between the upstream turn section 44 and the lumen input opening 18. According to embodiments of this presentation, 0.3% or less of the ultraviolet light radiation output from the cleaning section 26 in the upstream direction is output from opening 18 with turn section 44. According to embodiments of this presentation, 0.05% or less of the ultraviolet light radiation in output of the cleaning section 26 is output from opening 18 with a turn section having non-reflective walls. According to embodiments of this presentation, 0% of the ultraviolet light radiation in output of the cleaning section 26 is output from opening 18 with a turn section having reflective walls and an input muffler.

According to embodiments of this presentation, the apparatus 10 also comprises a flexible input air duct 48 having a second air duct input opening 50 and a second air duct output opening 52; the second air duct output opening 52 being connected to the lumen input opening 18, such that air flow 23 is input from the second air duct input opening 50. Flexible air duct 48 can also be extendable. Flexible air duct 48 can be particularly useful when it is desired to remove quickly the air from a particular portion of a room or movie set to replace the removed air with bioaerosol-free air. According to embodiments of this presentation (not shown), the input muffler 42 or an additional input muffler can be arranged in input of the flexible air duct 48.

According to embodiments of this presentation, the ventilator 22 is arranged upstream of the upstream turn section 44 of the lumen 16.

According to embodiments of this presentation, ventilator 22 is arranged upstream of the cleaning section 26 of the lumen 16. According to an embodiment of this presentation, the ventilator 22 comprises a fan arranged within the lumen. According to an embodiment, the fan 22 is powered by an electric motor. According to an embodiment, the ventilator 22 comprises a bladeless air multiplier. According to an embodiment, the ventilator 22 causes the air flow 23 to rotate along an axis of said lumen 16; said walls 14 of said lumen being arranged to favor said air flow rotation, for example with gun-barrel like grooves. According to embodiments of this presentation, the ventilator 22 is arranged in a sound muffling enclosure 54.

Figure 2:
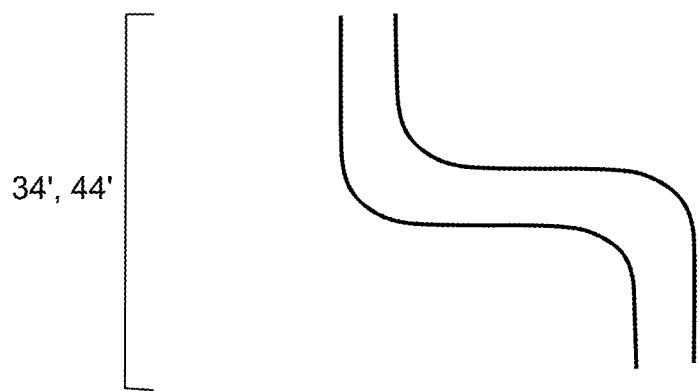
FIG. 2 illustrates an alternative turn section according to embodiments of this presentation.

FIG. 2 illustrates an alternative turn section 34', 44' that can be used in replacement of any of turn sections 34 or 44 as described above. Turn sections 34', 44' comprise two straight portions separated by a s-shaped curved portion that changes the direction of the air flow first by +90 degrees, then by −90 degrees. As turn sections 34, 44, turn sections 34', 44' are arranged between a lumen opening and the cleaning section 26, for changing a direction of the air flow 23 at least once such that no ultraviolet light emitted in the cleaning section 26 can exit the opening in direct line. Preferably, the turn sections are arranged such that that no ultraviolet light emitted in the cleaning section 26 is detectable from the lumen opening. Preferably, the inner walls of the turn sections are non-reflective to UV light. According to embodiments of this presentation, a sound-damping, non-reflective to UV light material can for example be used to line at least a portion of the turn sections.

Figure 3:
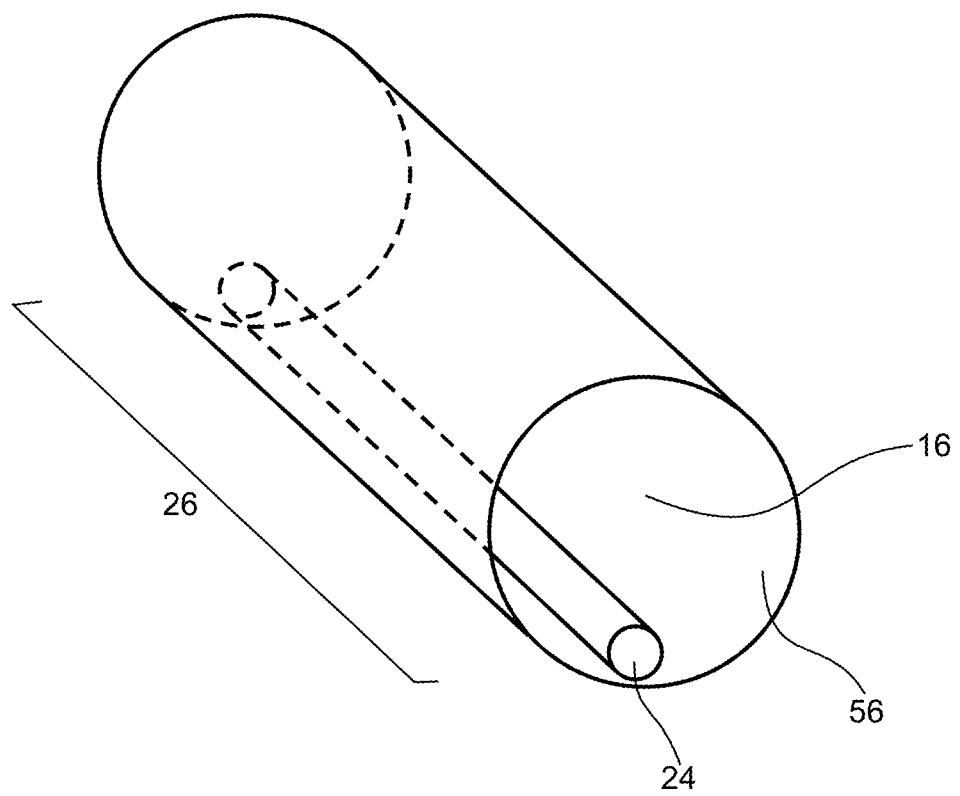
FIG. 3 illustrates a cleaning section of an apparatus according to embodiments of this presentation.

FIG. 3 illustrates an embodiment of cleaning section 26, wherein the lumen 16 has a circular cross section, and wherein the source of ultraviolet light 24 comprises at least one ultraviolet light bulb or tube arranged on a first wall portion of the cleaning section 26 of lumen 16. A material 56 reflective of ultraviolet light can be arranged on a second wall portion of said cleaning section 26 of said lumen 16. According to an embodiment of this presentation, a sum of said first and second wall portions forms the integrality of the lumen walls of the cleaning section 26 of lumen 16. Source 24 is arranged such that no shadow zone exists in section 26, such that any molecule of air traveling through section 26 is irradiated with LV light.

Figure 4:
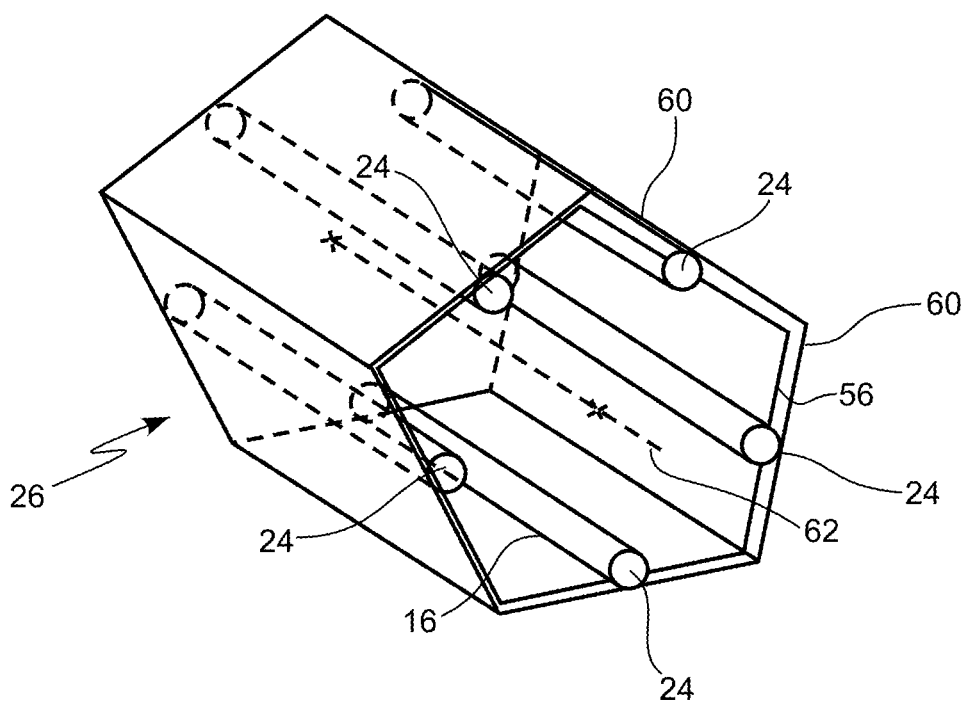
FIG. 4 illustrates a cleaning section of an apparatus according to embodiments of this presentation.

FIG. 4 illustrates another embodiment of a cleaning section of 26 that has a polygonal cross-section, wherein the lumen walls of cleaning section 26 form a juxtaposition of flat rectangular walls 60 elongated along an axis 62 of the lumen 16. According to an embodiment of this presentation, each of said rectangular walls 60 has a surface 56 reflective of ultraviolet light, and at least one of said rectangular walls 60 bears an ultraviolet light tube lamp source 24. A five-side polygonal cross section is illustrated, but n sides can be used, with n comprised between 3 and 8. As in the embodiment of FIG. 3, source 24 is arranged such that no shadow zone exists in section 26, such that any molecule of air traveling through section 26 is irradiated with UV light. This allows irradiating with ultraviolet light all the air passing through said lumen 16 along cleaning section 26. According to an embodiment of this presentation, any surface of the section 26 receives an ultraviolet radiation of 4500 microwatt/cm2 or more.

Figure 5:
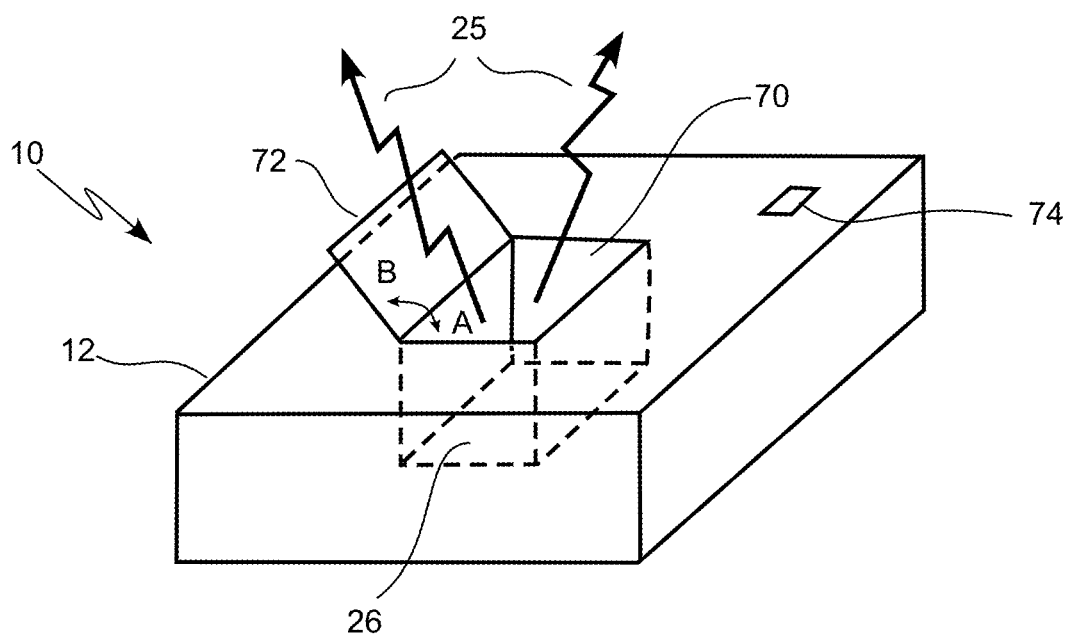
FIG. 5 illustrates an apparatus according to embodiments of this presentation.

FIG. 5 illustrates an apparatus 10 according to embodiments of this presentation wherein, in addition to the features detailed above, at least one portion of the lumen walls within the cleaning section 26 comprise a wall opening 70 with a mobile lid 72 having a closed position A and an open position B. According to such embodiments, lid 72 is so arranged that, when in the closed position A, the ultraviolet light 25 emitted by source 24 (not shown in FIG. 5) does not exit said lumen 16 through wall opening 70, and when in the open position B, the ultraviolet light 25 exits lumen 16 through wall opening 70. According to an embodiment, the ventilator 22 is inactivated when the lid 72 is in the open position B. According to an embodiment, the mobile lid 72 is remotely operable between its closed and open positions. According to an embodiment, apparatus 10 comprises a motion detector 74 that is arranged to shut of power to the source of ultraviolet light 24 if motion is detected by the motion detector. According to an embodiment, apparatus 10 comprises a timer that causes the apparatus 10 to operate with the lid 72 in the open position at predetermined times. One mobile lid 72 is illustrated in FIG. 5, but two or more mobile lids 72, arranged symmetrically around opening 70, can be used. According to embodiments of this presentation, lid 72 can be of a camera shutter-type.

According to an embodiment of this presentation, lid 72 can be made of a material that blocks UV light but not other wavelength, at least a portion of an inside surface of lid 72 being coated with a material that emits non-UV light when excited with UV light. For example, lid 72 can be made of glass and can have its inner (facing the inside of the lumen) surface coated with a fluorescent material such as phosphorous to emit visible light when excited by UV light. According to this embodiment, when excited by the UV light emitted by source 24, the phosphorous coating on the inner side of lid 72 emits visible light through lid 72, toward the outside of apparatus 10, whereby lid 72 operates as a source of visible light illuminating the outside of apparatus 10 when in the closed position and when the UV source of light 24 is activated.

Figure 6:
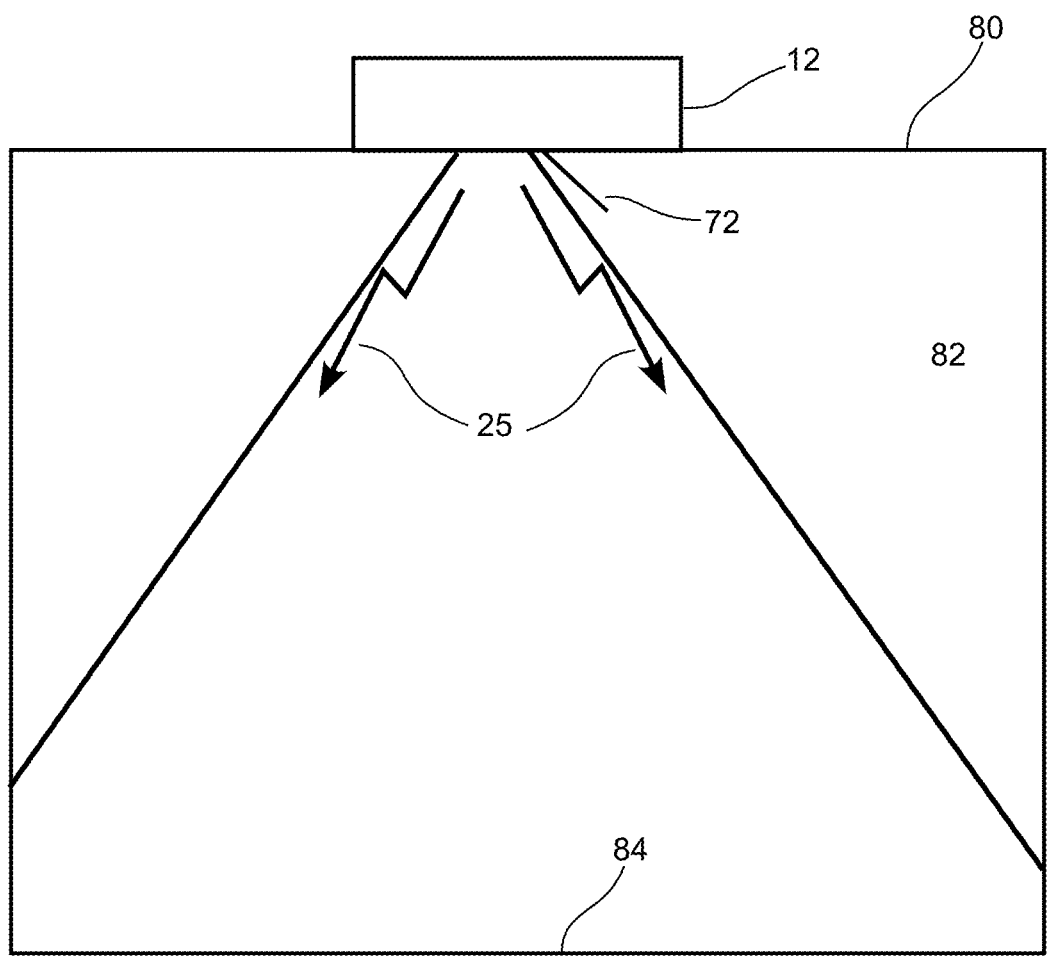
FIG. 6 illustrates an operation of the apparatus of FIG. 5.

As illustrated in FIG. 6, according to an embodiment, the enclosure 12 is arranged for being mounted within a wall or ceiling 80 of a room 82, and lid 72 is arranged such that when lid 72 is in the open position, ultraviolet light 25 irradiates at least a portion of a floor 84 or wall of said room opposite said apparatus 10/enclosure 12. In the above embodiment where lid 72 operates as a source of light, the enclosure 12 is also arranged such that when lid 72 is in the closed position (not shown in FIG. 6), reference 25 illustrates visible light that is produced by the coating of lid 72 and that illuminates at least a portion of a floor 84 or wall of said room opposite said apparatus 10/enclosure 12.

Room 82 can be a dentist office, a conference room, a school room etc. Apparatus 10 inactivates bioaerosol thoroughly and quietly when the room is occupied, but when the room empties, a user can e.g. press a button and the mobile lids 72 open out to expose the UVC lights and radiate directly on surfaces below the light. Apparatus 10 according to this embodiment has the dual purpose to dean air and then, under controlled conditions, clean surfaces. In a Dentist Office, the air is kept dean as droplets spew out of the patients mouth during cleaning for example. Then when the procedure is finished, the room can be vacated for 5 minutes, the apparatus 10 is opened up to exposure to the room and the surfaces are sanitized by ultraviolet light 25.

Figure 7:
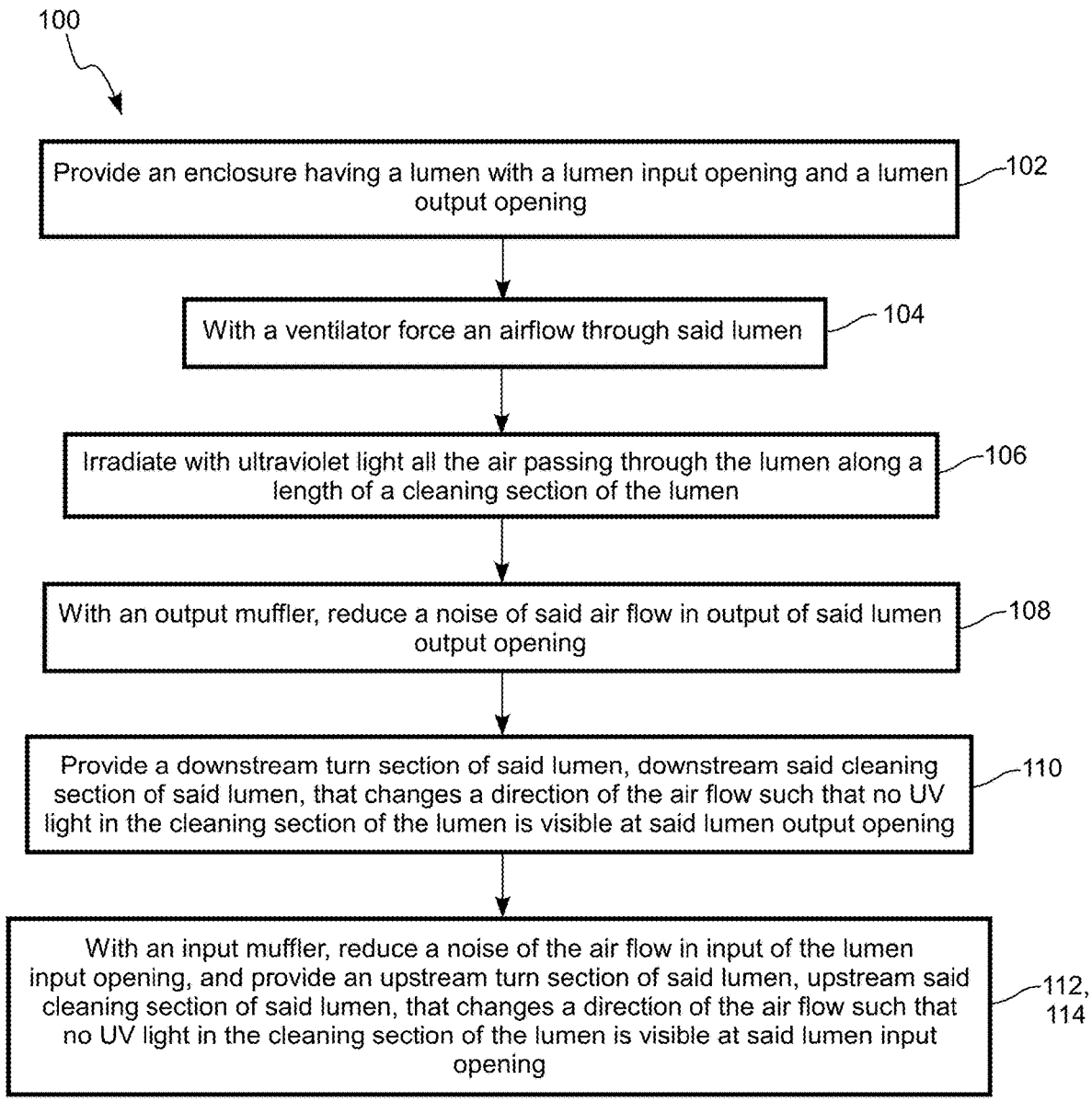
FIG. 7 illustrates a method according to embodiments of this presentation.

FIG. 7 illustrates a method 100 for inactivating bioaerosol in air according to embodiments of this presentation, the method comprising:

providing 102 an enclosure 12 having lumen walls 14 forming a lumen 16, said lumen having a lumen input opening 18 and a lumen output opening 20;

with a ventilator 22, forcing 104 an air flow 23 through said lumen 16;

in a cleaning section 26 of said lumen 16, irradiate 106 with ultraviolet light all the air passing through said lumen 16 along a length of said cleaning section 26;

with an output muffler 28, reducing 108 a noise of said air flow 23 in output of said lumen output opening 20; and providing 110 a downstream turn section 34 of said lumen 16, downstream said cleaning section 26 of said lumen, said downstream turn section 34 being arranged for changing a direction of said air 23 flow such that no ultraviolet light in said cleaning section 26 of said lumen is detectable at said lumen output opening 20.

According to embodiments of this presentation method 100 further comprises using an input muffler 42 to reduce 112 a noise of said air flow 23 in input of said lumen input opening 18, and providing 114 an upstream turn section 44 of said lumen 16, upstream said cleaning section 26 of said lumen 16, for changing a direction of said air flow 23 such that no ultraviolet light in said cleaning section 26 of said lumen 16 is detectable at said lumen input opening 18.

According to embodiments of this presentation, the method described above comprises tuning in combination the ventilator and US light source for killing or inactivating between 99.99% and 99.9999% of the bacteria, fungal spores or viruses aerosolized in an air flow 23 (i.e. inactivating the bioaerosol in the air) having a debit comprised between 200 cfm and 1600 cfm while producing with apparatus 10 a noise comprised between 18 dB and 35 dB.

Modifications, additions, or omissions may be made to the systems, apparatuses, and methods described herein without departing from the scope of the inventive concepts. The components of the systems and apparatuses may be integrated or separated. Moreover, the operations of the systems and apparatuses may be performed by more, fewer, or other components. The methods may include more, fewer, or other steps. Additionally, steps may be performed in any suitable order. As used in this document, "each" refers to each member of a set or each member of a subset of a set.

To aid the Patent Office, and any readers of any patent issued on this application in interpreting the claims appended hereto, applicants wish to note that they do not intend any of the appended claims or claim elements to invoke paragraph 6 of 35 U.S.C. Section 112 as it exists on the date of filing hereof unless the words "means for" or "step for" are explicitly used in the particular claim.

What is claimed is:

1. An apparatus for inactivating bioaerosol, comprising:

an enclosure having lumen walls forming a lumen, said lumen having a lumen input opening and a lumen output opening;

a ventilator arranged for forcing an air flow through said lumen;

in a cleaning section of said lumen, a source of ultraviolet light arranged to irradiate with ultraviolet light all the air passing through said lumen along a length of said cleaning section;

an output muffler arranged for reducing a noise of said air flow in output of said lumen output opening; and a downstream turn section of said lumen, downstream said cleaning section of said lumen, arranged for changing a direction of said air flow such that no ultraviolet light in said cleaning section of said lumen is detectable at said lumen output opening and such that the cross section of the lumen, formed by the lumen walls, is not restricted between the cleaning section and the output opening; wherein:

said ventilator is arranged such that said air flow has a debit comprised between 200 cfm and 1600 cfm, and said output muffler is arranged such that the apparatus produces a noise comprised between 18 dB and 35 dB.

2. The apparatus of claim 1, wherein said output muffler comprises a sound damping material lining the lumen walls of an output muffler section of the lumen, downstream of said cleaning section of said lumen.

3. The apparatus of claim 1, wherein said cleaning section of the lumen and said source of ultraviolet light are arranged such that any particle traveling through cleaning section 26 receives an energy of between 40 and 160 microwatt·second per cm2 of surface of the particle.

4. The apparatus of claim 1, wherein said downstream turn section of said lumen comprises a first elbow section that changes the direction of the airflow by 180 degrees between said cleaning section of said lumen and said lumen output opening.

5. The apparatus of claim 4, wherein said output muffler comprises a sound damping material lining the lumen walls of an output muffler section of the lumen, between said first elbow section and said lumen output opening.

6. The apparatus of claim 5, comprising a flexible output air duct having a first air duct input opening and a second air duct output opening; the first air duct input opening being connected to the lumen output opening, such that said air flow is output from the first air duct output opening.

7. The apparatus of claim 1, comprising an input muffler arranged for reducing a noise of said air flow in input of said lumen input opening.

8. The apparatus of claim 1, wherein an upstream turn section of said lumen, upstream said cleaning section of said lumen, is arranged for changing a direction of said air flow such that no ultraviolet light in said cleaning section of said lumen is detectable at said lumen input opening.

9. The apparatus of claim 8, wherein said upstream turn section of said lumen comprises a second elbow section that changes the direction of the airflow by 180 degrees between said lumen input opening and said cleaning section of said lumen.

10. The apparatus of claim 9, wherein said ventilator is arranged upstream of said upstream turn section of the lumen.

11. The apparatus of claim 9, comprising an input muffler arranged for reducing a noise of said air flow in input of said lumen input opening, comprising a sound damping material lining the lumen walls of an input muffler section of the lumen, between said upstream turn section and said lumen input opening.

12. The apparatus of claim 11, comprising a flexible input air duct having a second air duct input opening and a second air duct output opening; the second air duct output opening being connected to the lumen input opening, such that said air flow is input from the second air duct input opening.

13. The apparatus of claim 1, wherein the ventilator is arranged upstream of said cleaning section of said lumen.

14. The apparatus of claim 13, wherein the ventilator is arranged in a sound muffling enclosure.

15. The apparatus of claim 1, wherein the source of ultraviolet light comprises at least one ultraviolet light bulb arranged on a first wall portion of said cleaning section of said lumen, and a material reflective of ultraviolet light arranged on a second wall portion of said cleaning section of said lumen.

16. The apparatus of claim 1, wherein at least one portion of the lumen walls within said cleaning section of said lumen comprise a wall opening with a mobile lid having a closed position A and an open position B, wherein:

when said lid is in the closed position A, said ultraviolet light does not exit said lumen through said wall opening, and when said lid is in the open position B, said ultraviolet light exits said lumen through said wall opening.

17. The apparatus of claim 16, wherein said mobile lid is made of a material transparent to visible light and not to ultraviolet light, and comprises an inner surface coated with a material that emits visible light when exposed to ultraviolet light.

18. The apparatus of claim 1, wherein said cleaning section of the lumen and said source of ultraviolet light are arranged such that the intensity of the UV is comprised between 20.000 and 44.000 microwatt·second per cm2 of surface of the particle.

19. A method for inactivating bioaerosol, comprising:
   providing an enclosure having lumen walls forming a lumen, said lumen having a lumen input opening and a lumen output opening;
   with a ventilator, forcing an air flow through said lumen;
   in a cleaning section of said lumen, irradiate with ultraviolet light all the air passing through said lumen along a length of said cleaning section;
   with an output muffler, reducing a noise of said air flow in output of said lumen output opening; and
   providing a downstream turn section of said lumen, downstream said cleaning section of said lumen, said downstream turn section being arranged for changing a direction of said air flow such that no ultraviolet light in said cleaning section of said lumen is detectable at said lumen output opening and such that the cross section of the lumen, formed by the lumen walls, is not restricted between the cleaning section and the output opening;
   the method comprising: arranging said ventilator such that said air flow has a debit comprised between 200 cfm and 1600 cfm, and arranging said output muffler such that the apparatus produces a noise comprised between 18 dB and 35 dB.

20. The method of claim 19, comprising arranging said cleaning section of the lumen and said source of ultraviolet light such that any particle traveling through cleaning section 26 receives an energy of between 40 and 160 microwatt·second per cm2 of surface of the particle.

21. The method of claim 19, comprising using an input muffler to reduce a noise of said air flow in input of said lumen input opening, and providing an upstream turn section of said lumen, upstream said cleaning section of said lumen, for changing a direction of said air flow such that no ultraviolet light in said cleaning section of said lumen is detectable at said lumen input opening.

* * * * *